United States Patent [19]

Schulte-Elte et al.

[11] 4,179,448

[45] Dec. 18, 1979

[54] SPIRANE DERIVATIVES USEFUL AS PERFUMING AND FLAVOR-MODIFYING INGREDIENTS

[75] Inventors: Karl-Heinrich Schulte-Elte; Peter Fankhauser, both of Onex; Günther Ohloff, Bernex, all of Switzerland

[73] Assignee: Firmenich, S.A., Geneva, Switzerland

[21] Appl. No.: 841,124

[22] Filed: Oct. 11, 1977

[51] Int. Cl.$^2$ ............................................. C07D 307/94
[52] U.S. Cl. ............................... 260/346.11; 131/17 R; 252/522; 260/586 R; 424/285; 426/536
[58] Field of Search ..................................... 260/346.11

[56] References Cited

U.S. PATENT DOCUMENTS 4,014,905  3/1977  Skorianetz et al. ............... 260/347.4

OTHER PUBLICATIONS

Renold et al., Chemical Abstracts, vol. 84 (1976), 43818z.
Renold et al., Chemical Abstracts, vol. 87 (1977), 73246r.

*Primary Examiner*—Richard Raymond
*Attorney, Agent, or Firm*—Scully, Scott, Murphy & Presser

[57] ABSTRACT

New spirane derivatives useful as odor- and flavor-modifying ingredients for preparing perfumes, perfumed products, for the manufacture of artificial flavors or for flavoring foodstuffs, animal feeds, beverages, pharmaceutical preparations and tobacco products.

3 Claims, No Drawings

SPIRANE DERIVATIVES USEFUL AS PERFUMING AND FLAVOR-MODIFYING INGREDIENTS

THE INVENTION

The invention relates to new spirane derivatives having the formula

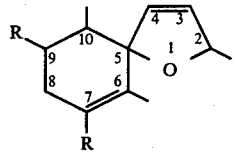
I wherein one of the symbols R represents a methyl group and the other a hydrogen atom, as well as to a perfume and flavour-modifying composition comprising a compound of formula I as an active ingredient.

The invention further relates to a method for improving, enhancing or modifying the organoleptic properties of perfumed products, or of foodstuffs, feedstuffs, beverages, pharmaceutical preparations or tobacco products which comprises adding thereto a small but effective amount of a compound of formula I, as defined hereinabove.

The invention also relates to a process for preparing compounds of formula I as defined hereinabove, which comprises reacting an alicyclic ketone of formula

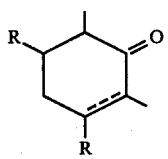
II possessing either a single or a double bond in the position indicated by the dotted line and wherein one of the symbols R represents a methyl group and the other a hydrogen atom, with but-1-yn-3-ol in the presence of a base when the said dotted line represents a single bond, or with an organometallic derivative thereof when the said dotted line represents a double bond, to afford a compound of formula

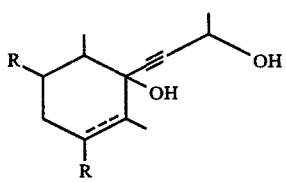
III wherein the dotted line and the symbols R are defined as hereinabove, reducing the triple bond of the compound of formula III wherein the dotted line represents a double bond by means of a hydrogenation in the presence of a partially deactivated catalyst and finally treating the thus obtained hydrogenation product with an acidic reagent; or treating the compound of formula III wherein the dotted line represents a single bond with an acidic reagent to afford the compound of formula I in admixture with a compound having the formula

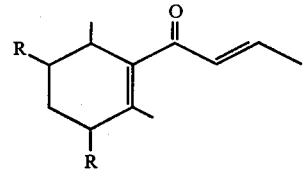
IV wherein the symbols R are defined as hereinabove and finally separating the constituents of the thus obtained mixture by means of a fractional distillation.

BACKGROUND OF THE INVENTION 2,6,10,10-Tetramethyl-1-oxa[4.5]deca-3,6-diene, having the formula

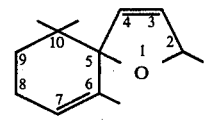

was described in the art several years ago, for example in Swiss Pat. No. 544,733. Whereas the above compound does not present any interest for the man in the art, at least with respect to its organoleptic properties, we have now found surprisingly that the isomeric derivatives of formula I possess interesting organoleptic properties and, consequently, they can be advantageously used as odour- and flavour-modifying ingredients.

PREFERRED EMBODIMENTS OF THE INVENTION

In the field of perfumery, compounds I are characterized by their original and powerful odour which presents a fresh, green, natural and flowery note reminiscent of that of mint leaves, clary sage, or even black currant in certain instances. Moreover, compounds I possess a fruity note reminiscent of that of citrus fruits such as grapefruits, for example.

Owing to the particular richness and complexity of its scent, which according to prior knowledge is quite exceptional for this type of derivative, compounds I can be widely used. They may enter in the preparation of various perfume compositions such as, for example, chypre, fruity, woody, flowery, rose, "fougère" or lavender-like compositions. Compounds I are moreover much appreciated for creating masculine-type compositions wherein they develop a particularly pleasant fresh and natural character.

The olfactive effects which can be achieved by making use of compounds I depend on the concentration used, as well as on the nature of the other coingredients to which they are admixed in a given perfume composition. Interesting effects can be achieved by the use of proportions of the order of 0.05% by weight of the compounds of the invention based on the total weight of the said composition. More typical effects are achieved by using proportions comprised between about 0.1 and 5% (parts by weight) of the said composition. Higher proportions, up to 20% or even more, can be used when particular olfactive effects are desired.

Compounds I can also be used advantageously as a sole ingredient or in admixture with at least one other perfuming ingredient and/or a suitable diluent or carrier for the preparation of perfumed products such as, for example, soaps, detergents, household materials or cosmetic preparations.

In the field of flavours, compounds I are characterized by their fruity gustative note, at the same time green and woody, reminiscent of the taste of black currant. Compounds I can therefore be advantageously used for the preparation of various artificial flavours, for example, fruit flavours such as black currant, raspberry or other red berry flavours, or even mint flavour. In the aroma compositions in which they are incorporated, compounds I develop, in most cases, a fresh, herbal and fruity gustative note which improve the natural character of said compositions.

Compounds I may thus be widely used, especially for flavouring foodstuffs, feedstuffs, beverages, pharmaceutical preparations or even tobacco products. Gustative effects such as those described above can be achieved by using proportions of compounds I comprised in between about 0.01 and 10 ppm (parts per million) by weight of the flavoured material.

Preferred proportions are comprised in between about 0.1 and 2.0, in certain cases 5.0, ppm. Proportions higher that the above given upper limit may also be used when particular gustative effects are desired.

2,6,7,10-Tetramethyl-1-oxa-spiro[4.5]deca-3,6-diene and 2,6,9,10-tetramethyl-1-oxa-spiro[4.5]deca-3,6-diene, which are novel compounds, can be prepared according to the process described hereinabove.

In accordance with one of the embodiments of the process of the invention, 2,5,6-trimethyl-cyclohex-2en-1-one and 2,3,6-trimethyl-cyclohex-2-en-1-one—i.e. the compounds of formula II wherein the dotted line represents a double bond—can be converted into 2,6,9,10-tetramethyl-1-oxa-spiro[4.5]deca-3,6-diene and 2,6,7,10-tetramethyl-1-oxa-spiro[4.5]deca-3,6-diene, respectively. Such a synthetic method may be illustrated as follows

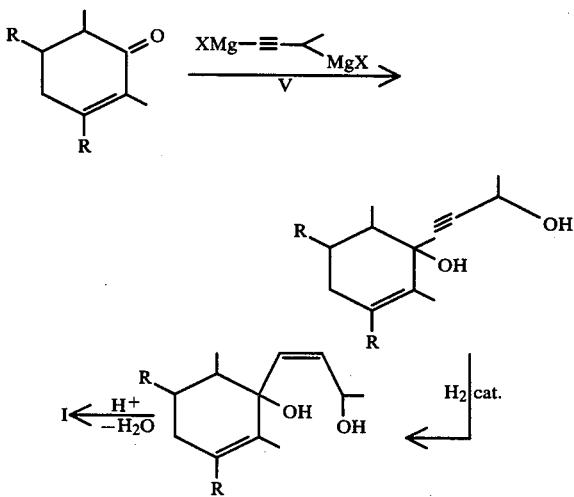

In the above reaction scheme, X defines a halogen atom such as Cl, Br or I.

In accordance with a further embodiment of the present process, mixtures in various proportions of 2,6,9,10-tetramethyl-1-oxa-spiro[4.5]deca-3,6-diene and 2,6,7,10-tetramethyl-1-oxa-spiro[4.5]deca-3,6-diene may be easily prepared from 2,3,6-trimethyl-cyclohexanone—i.e. the compound of formula II wherein the dotted line represents a single bond—by reacting this latter compound with but-1-yn-3-ol according to the method described in Swiss Pat. No. 544,733. The relative proportions of the constituents of the obtained mixtures may vary within wide limits, depending on the reaction conditions or on the method of purification.

Each of the reaction steps of the above process may be effected in accordance with the usual techniques and will be described in a more detailed way in the examples given hereinbelow.

Alicyclic ketones II, used as starting materials, are commercially available products. Said compounds can also be prepared from known compounds according to the usual techniques.

It has to be noted that the described formula is deemed to define all possible spiranic stereoisomers of compounds I. For practical and economical reasons, compounds I are used in the form of a mixture of stereoisomers, as directly obtained from the above described process.

The examples given hereinafter illustrate, but not limit, the present invention. In the said examples, the temperatures are given in degrees centigrade and the abbreviations have the definition usual in the art.

EXAMPLE 1

2,6,9,10-Tetramethyl-1-oxa-spiro[4.5]deca-3,6-diene (a) to a cold (0°) mixture of 65 g of methyl iodide, 14.4 g of magnesium turnings and 150 ml of anhydrous ether there was added dropwise a solution of 21 g of but-1-yn-3-ol in 50 ml of anhydrous ether. The reaction mixture was further stirred for 2 hours, then let to heat to room temperature and finally reacted with 35 g of 2,5,6-trimethyl-cyclohex-2-en-1-one in 75 ml of anhydrous ether. After having been heated at reflux for 3 hours and then cooled to room temperature, the reaction mixture was hydrolyzed by means of a saturated aqueous solution of $NH_4Cl$. After separation of the organic layer, washing, drying, and distillation, there were obtained 40 g (80%) of 1-hydroxy-2,5,6-trimethyl-1-(but-1-yn-3-hydroxy-1-yl)-cyclohex-2-ene, b.p. 100°–110°/0.2 Torr.

IR: 3350, 2200 cm$^{-1}$.

NMR: 0.8–2.2 (6H, 2s); 1.38 (1H, d, J=6.5 cps); 1.42 (1H, d, J=6.5 cps); 1.78 (3H, m); 4.45 (1H, m); 5.3 (1H, m) δ ppm.

(b) a solution of 31.5 g of the above compound in 350 ml of methanol was hydrogenated at room temperature and under atmospheric pressure, in the presence of 0.5 g of LINDLAR catalyst (partially deactivated Pd catalyst). After consumption of 3.1 liters of hydrogen, filtration and evaporation, there were obtained 30.8 g (95%) of 1-hydroxy-2,5,6-trimethyl-(1-but-1-en-3-hydroxy-1-yl)-cyclohex-2-ene. The compound thus prepared was used for the subsequent reaction step without any further purification.

(c) to a cold (0°) solution of 7 g of the above compound in 50 ml of petroleum ether (b.p. 30°–50°), there were added dropwise, under nitrogen atmosphere, 5 ml of aqueous 30% $H_2SO_4$. The reaction mixture was further stirred for 1 hour, then neutralized by means of $NaHCO_3$, washed and dried. From the organic layer there were obtained upon distillation, 5.7 g (85%) of 2,6,9,10-tetramethyl-1-oxa-spiro[4.5]deca-3,6-diene.

IR: 3070, 3020, 1100-1000, 875, 808, 755, 718 cm$^{-1}$.

NMR: 0.8–1.1 (6H); 1.26 (3H, d, J=6.5 cps); 1.29 (3H, d, J=6.5 cps); 1.57 (3H, m); 5.32 (1H, m); 5.54 (2H, m); 5.78 (2H, m) δ ppm.

MS: M$^+$=192; m/e=177, 159, 136, 121, 109, 93, 77, 43.

2,6,7,10-Tetramethyl-1-oxa-spiro[4.5]deca-3,6-diene (a') The following reactants were treated in the conditions given sub letter (a) hereinabove:
21.9 g of magnesium turnings
98 g of ethyl bromide in 250 ml of anhydrous tetrahydrofurane (THF)
31.5 g of but-1-yn-3-ol in 250 ml of anhydrous THF
41.4 g of 2,3,6-trimethyl-cyclohex-2-en-1-one There were thus obtained 39.4 g (80%) of 1-hydroxy-2,3,6-trimethyl-1-yn-3-hydroxy-1-yl)-cyclohex-2-ene, m.p. 114°–123°.

IR: 3575, 3400 cm$^{-1}$.

NMR: 1.08 (3H, d, J=6.5 cps); 1.42 (3H, d, J=7 cps); 1.62 (3H, s); 1.6–2.2 (8H, m); 2.70 (1H, broad s); 3.05 (broad s); 4.50 (1H, m) δ ppm.

MS: m/e=190, 175, 157, 142, 131, 115, 105, 91, 79, 69, 55, 43.

(b') 37.4 g of the above compound in 300 ml of ethyl alcohol were hydrogenated at room temperature and under atmospheric pressure in the presence of 2 g of palladium catalyst (5% on charcoal) and 0.2 g of quinoline. After consumption of the theoretical amount of hydrogen and treatment as described sub letter b, there were obtained 37.8 g (100%) of 1-hydroxy-2,3,6-trimethyl-1-(but-1-en-3-hydroxy-1-yl)-cyclohex-2-ene.

(c') 37.8 g of the above compound were reacted as described sub letter (c) with 10 ml of aqueous 30% $H_2SO_4$ to afford 27.8 g (80%) of 2,6,7,10-tetramethyl-1-oxa-spiro[4.5]deca-3,6-diene, b.p. 53°–54°/0.2 Torr.

IR: 3060, 1665 cm$^{-1}$.

NMR: 0.82 (3H, d, J=6 cps); 1.26 (3H, d, J=7 cps); 1.49 (3H, s); 1.63 (3H, s); 1.5–2.2 (5H, m); 4.85 (1H, q, J=6 cps); 5.41 (1H, m); 5.72 (1H, d, J=6 cps) δ ppm.

MS: M$^+$=192; m/e=177, 159, 150, 135, 123, 107, 91, 79, 67, 55, 43.

2,3,6-Trimethyl-cyclohex-2-en-1-one used hereinabove as starting material was prepared from 2,5,6-trimethyl-cyclohex-2-en-1-one after treatment of the latter by means of p-toluenesulfonic acid (3–5%) at 150°, in the presence of an excess of ethylene-glycol. The desired compound, which is obtained in a 85% yield, was found identical to a sample prepared according to J. Org. Chem. 37, 2340 (1972).

EXAMPLE 2

2,6,7,10-Tetramethyl-1-oxa-spiro[4.5]deca-3,6-diene
and
2,6,9,10-Tetramethyl-1-oxa-spiro[4.5]deca-3,6-diene (a) To a mixture of 45 g of sodium hydroxide and 150 ml of anhydrous ether there were added, under stirring and external cooling, 28 g of 2,3,6-trimethyl-cyclohexanone and 16 g of but-1-yn-3-ol. After addition of the reactants, the mixture was heated for 16 hours, then cooled to room temperature and finally diluted with water. The separated organic layer finally gave, after distillation, 30.2 g (72%) of 1-hydroxy-2,3,6-trimethyl-1-(but-1-yn-3-hydroxy-1-yl)-cyclohexane, b.p. 105°–115°/0.02 Torr.

(b) 28.4 g of the above compound, mixed with 50 g of $H_3PO_4$ 60% in water, were heated at 70° for 6 hours. After cooling to room temperature the reaction mixture was extracted with petroleum ether (b.p. 30°–50°) and the organic layer washed with aqueous 5% $NaHCO_3$, then with water and finally distilled on a VIGREUX column. There were thus obtained 16 g of a reaction product (b.p. 45°–70°/0.02 Torr) containing, according to the vapour phase chromatography analysis, ca. 70% of the desired mixture and 30% of by-products.

The reaction mixture as obtained hereinabove was finally submitted to a fractional distillation giving first 9.4 g of a 90:10 mixture of 2,6,9,10-tetramethyl-1-oxa-spiro[4.5]deca-3,6-diene and 2,6,7,10-tetramethyl-1-oxa-spiro[4.5]deca-3,6-diene, respectively (b.p. 53°–59°/0.01 Torr).

The above mentioned proportions are easily determined by mass spectrometry, after comparison of the fragmentation intensities at m/e=136 and 150, respectively.

A further fraction, having b.p. 65°–70°/0.2 Torr, was obtained from the above distillation and identified as a mixture of 2,5,6-trimethyl-1-butenoyl-cyclohex-1-ene and 2,3,6-trimethyl-1-butenoyl-cyclohex-1-ene, respectively.

IR: 1700-1620, 970 cm$^{-1}$.

NMR: 0.8–1.2 (6H); 1.48 (3H, s); 1.92 (3H, d of d, $J_1$=6 cps, $J_2$=3 cps); 5.9–7.0 (2H) δ ppm.

MS: M$^+$=192; m/e=177, 149, 135, 107, 91, 81, 69, 55, 41.

EXAMPLE 3

A base perfume composition was prepared by mixing the following ingredients (parts by weight):

| | |
|---|---|
| Linalool | 200 |
| Lavandin oil | 200 |
| Isononyl acetate | 150 |
| p-t-Butyl-cyclohexyl acetate | 100 |
| Di-isobutylcarbinyl acetate | 100 |
| "Citrate" mint oil | 50 |
| Lemon oil | 30 |
| Methyl-ionone | 20 |
| Hydroxycitronellal | 20 |
| 4-Isopropyl-cyclohexylmethanol** | 10 |
| 1,1,-Dimethyl-4-acetyl-6-t-butylindane | 10 |
| Decylic aldehyde 10% | 10 |
| Total | 900 |

*in diethyl phthalate
**available from Firmenich SA, Geneva, Switzerland (see for example, British Patent No. 1,416,658).

The above base possesses a rather pleasant odour reminiscent of that of lavandin oil and may be conveniently used for the preparation of perfumed products such as shampoos or bubble baths, for example.

By adding to 70 g of the above base 30 g of a 10% solution of 2,6,9,10-tetramethyl-1-oxa-spiro[4.5]deca-3,6-diene in diethylphthalate, a new perfume composition possessing a fresher, more natural and more flowery odour than that of the above base was obtained.

When in the above example, 2,6,9,10-tetramethyl-1-oxa-spiro[4.5]deca-3,6-diene is replaced by an identical amount of 2,6,7,10-tetramethyl-1-oxa-spiro[4.5]deca-3,6-diene or of the mixture of 2,6,9,10-tetramethyl-1-oxa-spiro[4.5]deca-3,6-diene and 2,6,7,10-tetramethyl-1-oxa-spiro[4.5]deca-3,6-diene prepared in Example 2, analogous effects are observed.

EXAMPLE 4

A base perfume composition for a masculine Eau de Toilette was prepared by mixing the following ingredients (parts by weight):

| | |
|---|---|
| Bergamot oil dist. | 160 |
| p-t-Butyl-cyclohexylacetate | 100 |
| Galbanum resinoid 50%* | 80 |
| Absolute oak moss descolorized 50%* | 80 |

-continued

| | |
|---|---|
| Pentadecanolide 10%* | 80 |
| Cedryl acetate | 60 |
| Thibetine 10%* | 40 |
| Cedrene | 40 |
| Lemon oil | 40 |
| Vetiveryl acetate | 40 |
| Florida orange oil | 40 |
| α-Isomethylionone | 40 |
| Synthetic civette 10%* | 20 |
| Lavender oil | 20 |
| Oppoponax oil 10%* | 10 |
| Eugenol | 10 |
| Coriander oil | 10 |
| Nutmeg oil | 10 |
| 4-Isopropyl-cyclohexylmethanol** | 10 |
| α-Ionone | 10 |
| Total | 900 |

*in diethyl phthalate
**available from Firmenich SA, Geneva, Switzerland (see, for example, British Patent No. 1,416,658).

By adding to 90 g of the above base 5 g of 2,6,9,10-tetramethyl-1-oxa-spiro[4.5]deca-3,6-diene a new perfume composition with an odour possessing a better defined lifting character was obtained. The said odour, which is moreover richer than that of the above base, presents an original flowery note.

When, in the above example, 2,6,9,10-tetramethyl-1-oxa-spiro[4.5]deca-3,6-diene is replaced by an identical amount of 2,6,7,10-tetramethyl-1-oxa-spiro[4.5]deca-3,6-diene or of the mixture 2,6,9,10-tetramethyl-1-oxa-spiro[4.5]deca-3,6-diene and 2,6,7,10-tetramethyl-1-oxa-spiro[4.5]deca-3,6-diene prepared in Example 2, analogous effects are observed.

EXAMPLE 5

Two syrups of raspberry and black currant type, respectively, were prepared by diluting 1 part by weight of commercial syrup with 4 and 9 parts by weight, respectively, of water. The beverages thus obtained were flavoured with a proportion of 0.3 and 0.5 ppm, respectively, of 2,6,9,10-tetramethyl-1-oxa-spiro[4.5]deca-3,6-diene.

The flavoured beverages were subjected to organoleptic evaluation by a panel of experienced tasters whose judgment was expressed as follows:
 the flavoured raspberry syrup possessed an improved top note and an overall aroma which was fuller and fresher than that of the unflavoured syrup,
 the flavoured black currant syrup showed a fuller and a more natural taste than the unflavoured one. It possessed moreover a better defined herbal and fruity note.

When, in the above example, 2,6,9,10-tetramethyl-1-oxa-spiro[4.5]deca-3,6-diene is replaced by an identical amount of 2,6,7,10-tetramethyl-1-oxa-spiro[4.5]deca-3,6-diene or of the mixture of 2,6,9,10-tetramethyl-1-oxa-spiro[4.5]deca-3,6-diene and 2,6,7,10-tetramethyl-1-oxa-spiro[4.5]deca-3,6-diene prepared in Example 2, analogous effects are observed.

What we claim is:

1. A compound having the formula

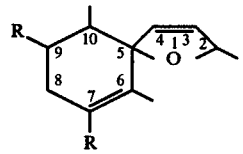

wherein one of the symbols R represents a methyl group and the other a hydrogen atom.

2. 2,6,9,10-Tetramethyl-1-oxa-spiro[4.5]deca-3,6-diene.

3. 2,6,7,10-Tetramethyl-1-oxa-spiro[4.5]deca-3,6-diene.

* * * * *

UNITED STATES PATENT AND TRADEMARK OFFICE
CERTIFICATE OF CORRECTION

PATENT NO. : 4,179,448
DATED : December 18, 1979
INVENTOR(S) : Schulte-Elte, et al.

It is certified that error appears in the above-identified patent and that said Letters Patent are hereby corrected as shown below:

Column 3, line 30, "cyclohex-2en-" should read
--cyclohex-2-en- --;

Column 5, line 11, "trimethyl-1-yn-3-hydroxy" should read
--trimethyl-1-(but-1-yn-3-hydroxy--;

Column 6, line 33, " "Citrate" mint oil " should read
--"Citrata" mint oil--; and Column 6, line 37, "Decyclic aldehyde 10%" should read
--Decyclic aldehyde 10%*--.

Signed and Sealed this

Sixth Day of May 1980

[SEAL]

Attest:

SIDNEY A. DIAMOND

Attesting Officer

Commissioner of Patents and Trademarks